(12) United States Patent
Chiu

(10) Patent No.: US 8,685,673 B2
(45) Date of Patent: Apr. 1, 2014

(54) METHOD FOR PRODUCING INDOLE DERIVATIVE

(75) Inventor: Hsien-Tai Chiu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 189 days.

(21) Appl. No.: 12/804,947

(22) Filed: Aug. 2, 2010

(65) Prior Publication Data

US 2012/0028309 A1    Feb. 2, 2012

(51) Int. Cl.
*C12P 19/26* (2006.01)
*C12P 17/14* (2006.01)
*C12N 1/20* (2006.01)
*C12N 15/00* (2006.01)
*C07H 21/04* (2006.01)

(52) U.S. Cl.
USPC ..... 435/84; 435/121; 435/252.3; 435/252.33; 435/320.1; 536/23.2

(58) Field of Classification Search
None
See application file for complete search history.

(56) References Cited

PUBLICATIONS

Nakanishi et al., "K-252b, c and d, Potent Inhibitors of Protein Kinsase C From Microbial Origin", The Journal of Antibiotics, vol. 39, No. 8, pp. 1066-1071 (1986).
Chen et al., "Functional Characterization and Substrate Specificity of Spinosyn Rhamnosyltransferase by in Vitro Reconstitution of Spinosyn Biosynthetic Enzymes", The Journal of Biological Chemistry, vol. 284, No. 11, pp. 7352-7363 (2009).
Gutierrez-Lugo et al., "Isolation of three new naturally occurring compounds from the culture of *Micromonospora* sp. P1068", Natural Product Research, vol. 19, No. 7, pp. 645-652 (2005).
Panda et al., "Synthesis of Novel Indolyl-Pyrimidine Antiinflammatory, Antioxidant and Antibacterial Agents", Indian Journal of Pharmaceutical Sciences, vol. 70, No. 2, pp. 208-215 (2008).
Chiu et al., "Biochemical characterization and substrate specificity of the gene cluster for biosyntheses of K-252a and its analogs by in vitro heterologous expression system of *Escherichia coli*", Molecular BioSystems, vol. 5, pp. 1192-1203 (2009).

*Primary Examiner* — Anand Desai
*Assistant Examiner* — Iqbal H Chowdhury
(74) *Attorney, Agent, or Firm* — Edwards Wildman Palmer LLP; Peter F. Corless, Esq.; Steven M. Jensen, Esq.

(57) ABSTRACT

The present invention provides a method for in vitro producing an indole derivative in a one-pot reaction. The method for producing a rhamnosylated indolocarbazole compound includes the steps of transforming a plasmid carrying a gene encoding N-glycosyltransferase into a bacterial strain; expressing the gene encoding N-glycosyltransferase in the bacterial strain; lysing the bacterial strain to obtain a crude enzyme extract; and adding TDP-glucose, an indolocarbazole aglycone and a metal ion in the crude enzyme extract for performing an enzymatic reaction to form the rhamnosylated indolocarbazole compound. Alternatively, the method for producing an indole-3-carboxaldehyde analog includes the steps of transforming a plasmid carrying a gene encoding NokA of *Nocardiopsis* sp. K-252 into a bacterial strain; expressing the gene encoding NokA in the bacterial strain; lysing the bacterial strain to obtain a crude enzyme extract; and adding an L-tryptophan analog for performing an enzymatic reaction to form the indole-3-carboxaldehyde analog.

10 Claims, 4 Drawing Sheets
(2 of 4 Drawing Sheet(s) Filed in Color)

METHOD FOR PRODUCING INDOLE DERIVATIVE

BACKGROUND OF THE INVENTION

1. Field of the Invention

The present invention relates to methods for producing an indole derivative, and more particularly to a method for producing a rhamnosylated indolocarbazole compound or an indole-3-carboxaldehyde analog.

2. Description of Related Art

The family of indolocarbazole natural products has been a valuable source of lead compounds with potential therapeutic applications in the treatment of cancer and neurodegenerative disorders. In the indolocarbazole family, lestaurtinib has been approved by FDA for treating acute leukemia, CEP-1347 has entered the phase III clinical trial for treating Parkinson's disease, and K-252a, K-252b and staurosporine display anti-cancer activities. In addition, it is known that K-252d, rhamnosyl-K252c, is capable of inhibiting activity of protein kinase C (PKC). The PKC family plays an important role in cellular proliferation and signal transduction. Hence, specific inhibitors against PKC are promising antitumor drugs for cancer chemotherapy.

S. Nakanishi et al. disclosed the extraction of K-252d from incubation medium of a microorganism. (J. Antibiot., 1986, 39, 1066-1071) However, such extraction needs three purification steps to obtain only 13.3 mg of K-252d from 8.4 L culture medium.

The synthesis of K-252d is summarized in the following Scheme I.

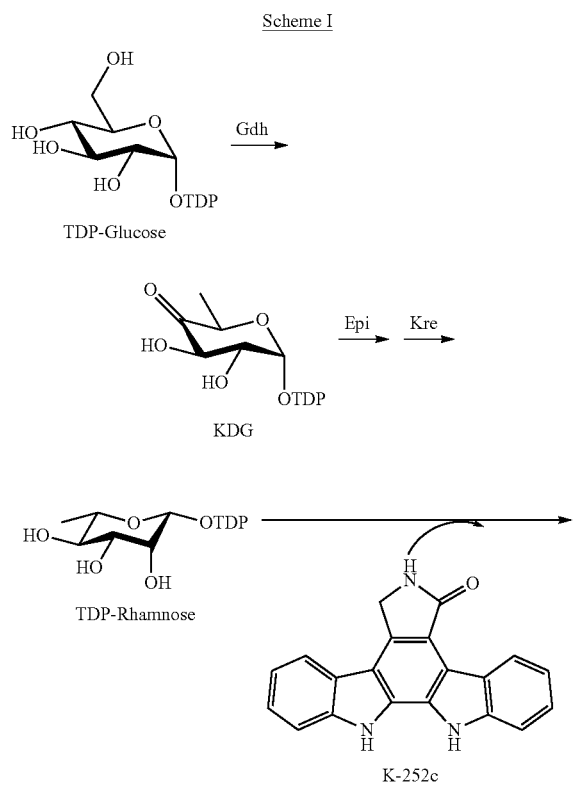

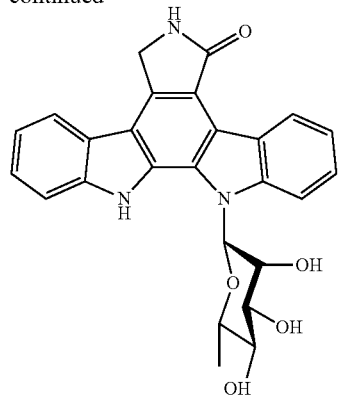

K-252d
(Rhamnosyl-K252c)

As shown in Scheme I, synthesis of TDP-rhamnose is accomplished by tandem enzymatic conversion of TDP-glucose with NDP-glucose 4,6-dehydratase (Gdh), NDP-4-keto-6-deoxyglucose epimerase (Epi) and NDP-4-ketorhamnose reductase (Kre). Then, TDP-rhamnose is linked to K-252c by N-glycosyltransferase to form K-252d.

Chen et al. disclosed in vitro biosynthesis of TDP-rhamnose. (J. Biol. Chem., 2009, 284, 7352-7363) However, this method needs to purify three enzymes, Gdh, Epi and Kre, and several processing steps.

In addition, it is known that indole-3-carboxaldehyde (ICA) has anti-bacterial activity to gram positive bacteria such as *S. aureus* or to gram negative bacteria such as *E. coli* or *E. faecium*. Further, ICA can be modified for treating stroke, cancer or neurodegeneration disease such as Parkinson's disease. A modified ICA, 3-ICA-TSC, is an amebacide.

However, it is very complicated to purify ICA from a microorganism. (Nat. Prod. Res., 2005, 19, 645-652) S. S. Panda et al. disclosed chemical synthesis of ICA, which may cause environmental problems due to usage of organic solvents and toxic agents. (Indian J. Pharm. Sci., 2008, 70, 208-215)

Therefore, in order to overcome the drawbacks of the conventional methods, the present invention provide a novel method for in vitro simply and efficiently producing an indole derivative.

SUMMARY OF THE INVENTION

The present invention provides a novel method for in vitro producing a rhamnosylated indolocarbazole compound. The method includes the steps of: transforming a plasmid carrying a gene encoding N-glycosyltransferase into a bacterial strain; expressing the gene encoding N-glycosyltransferase in the bacterial strain; lysing the bacterial strain to obtain a crude enzyme extract; and adding TDP-glucose, an indolocarbazole aglycone and a metal ion in the crude enzyme extract for performing an enzymatic reaction to form the rhamnosylated indolocarbazole compound.

Preferably, the bacterial strain is an *E. coli* strain, which is preferably incubated at 25-40□.

Preferably, the N-glycosyltransferase is NokL of *Nocardiopsis* sp. K-252.

In accordance with the present invention, the step of lysing is performed by a homogenizer (e.g. French press) or sonication.

In accordance with the present invention, the bacterial strain is lysed in a buffer selected from the group consisting of Tris buffer, HEPES buffer, MOPS buffer, $K_2HPO_4$ buffer and MES buffer. Preferably, pH of the buffer is in a range from 5 to 10, and the buffer contains 0-25% of glycerol.

In accordance with the present invention, the indolocarbazole aglycone is a compound of formula (I) or a compound of formula (II), or its analog

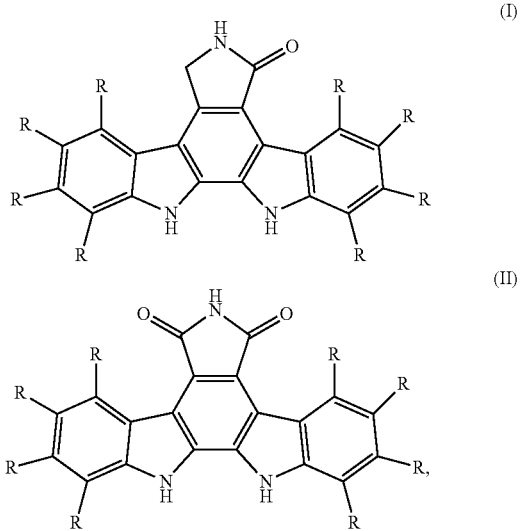

in which R═H, OH, F, Cl, Br or $CH_3$, and wherein the rhamnosylated indolocarbazole compound is K-252d (or its analogs).

In accordance with the present invention, the metal ion is a magnesium ion or a manganese ion, and the enzymatic reaction is performed at 4-40□.

In addition, the present invention provides a method for in vitro producing an indole-3-carboxaldehyde analog. The method includes the steps of: transforming a plasmid carrying a gene encoding NokA of *Nocardiopsis* sp. K-252 into an *E. coli* strain; expressing the gene encoding NokA in the *E. coli* strain; lysing the *E. coli* strain to obtain a crude enzyme extract; and adding an L-tryptophan analog of formula (III)

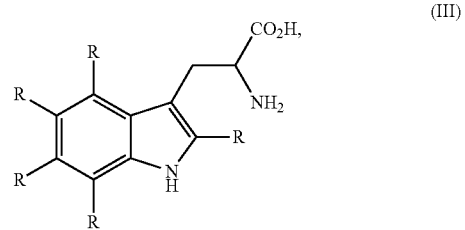

wherein R═H, OH, F, Cl, Br or $CH_3$. Preferably, the *E. coli* strain is lysed in a buffer selected from the group consisting of Tris buffer, HEPES buffer, MOPS buffer, $K_2HPO_4$ buffer and MES buffer, wherein pH of the buffer is in a range from 5 to 10, and the buffer contains 0-25% of glycerol.

In the following section preferred embodiments are described. However, this is not intended in any way to limit the scope of the present invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The present invention can be more fully understood by reading the following detailed description of the preferred embodiments, with reference made to the accompanying drawings, wherein.

DETAILED DESCRIPTION OF PREFERRED EMBODIMENTS

Figure 1:
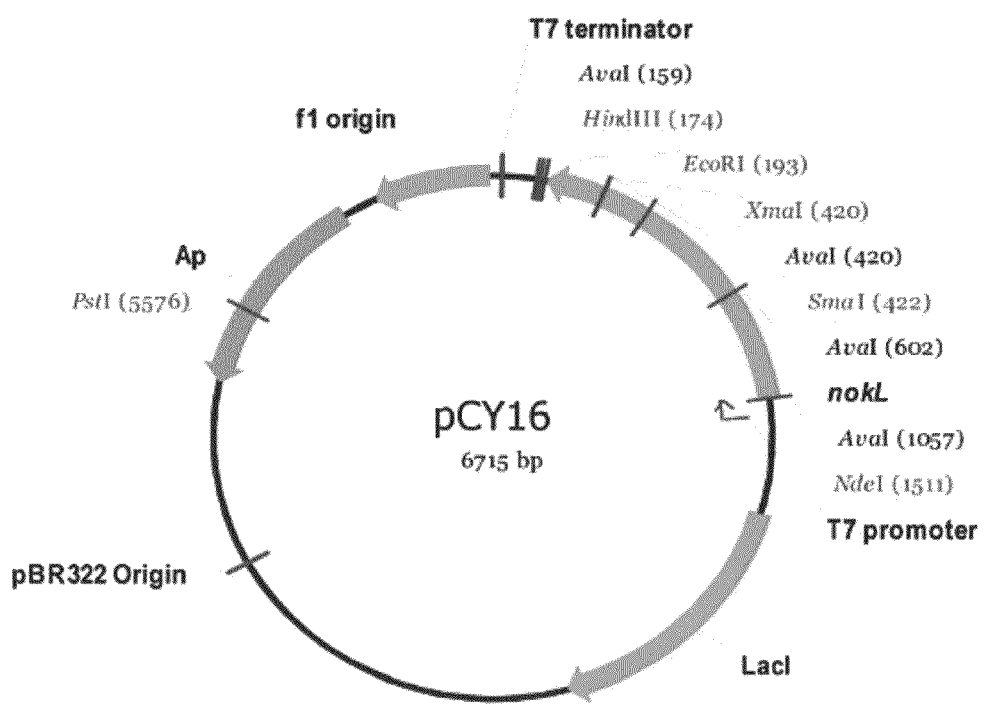
FIG. 1 is a construct map of pCY16 according to the present invention.

The following illustrative embodiments are provided to illustrate the disclosure of the present invention, these advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

It is known that *Nocardiopsis* sp. K-252 (*Nonomuraea longicatena* K252T, NRRL15532) produces indolocarbazole alkaloids of antitumor antibiotics. Thus, the inventors constructed a fosmid genomic DNA library of *Nocardiopsis* sp. K-252 by using a CopyControl fosmid library production kit (Epicentre). As a result, the genomic library was constructed with a total of 5856 fosmid clones, whereas the average sizes of genomic DNA fragments were ca. 35 kb per clone. A 45 kb sequence contig was subsequently obtained by DNA sequencing to cover the entire gene cluster for the biosynthesis of the indolocarbazole compounds, K-252a and its analogs, in *Nocardiopsis* sp. K-252. The DNA sequence of nok genes responsible for biosynthesis of K-252a was deposited in GenBank under accession number FJ031030. Sequence analysis of the 45 kb genomic sequence revealed 35 open reading frames. The inventors identified the gene nokL (SEQ ID NO: 1; GenBank accession number: ACN29718) encoding N-glycosyltransferase, and the gene nokA (SEQ ID NO: 2; GenBank accession number: ACN29719) encoding L-amino acid oxidase. The detailed description about molecular cloning, sequence analysis and functional characterization of the gene cluster for biosynthesis of K-252a and its analogs has been published on Mol. BioSyst., 2009, 5, 1180-1191, which is entirely incorporated herein by reference.

The present invention provides a heterologous expression system of *Escherichia coli* containing indolocarbazole N-glycosyltransferase for in vitro producing molecules exhibiting potent neuroprotective or broad anticancer activities in a one-pot reaction.

In the present invention, the plasmid containing the DNA encoding N-glycosyltransferase is transformed into an *E. coli* strain, which is then incubated until $OD_{600}$ being 0.3-0.7.

Preferably, the N-glycosyltransferase is NokL of *Nocardiopsis* sp. K-252. After adding an inducing agent, the bacterial culture is further incubated at a 25-40□. Then, the culture pellet is collected and further re-suspended in a buffer solution to be lyzed by a homogenizer (e.g. French press) or sonication, such that the crude enzyme extract is obtained. Preferably, the buffer solution is Tris, HEPES, MOPS, $K_2HPO_4$ or MES, the pH value of the buffer solution is in the range from 5 to 10, and the glycerol concentration of the buffer solution is 0-25%.

Subsequently, the crude enzyme extract is mixed with TDP-glucose, indolocarbazole aglycone, K-252c or its analog, and metal ions. The indolocarbazole aglycone is the compound of formula (I) or the compound of formula (II), in which R=H, OH, F, Cl, Br or $CH_3$. The metal ions are magnesium ions or manganese ions. The enzymatic biosynthesis is performed at 4-40° C.

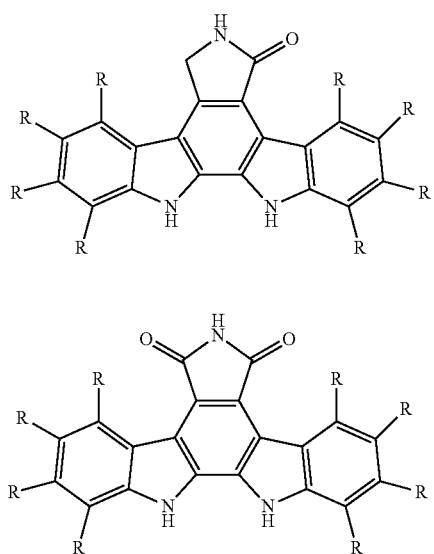

In addition, the present invention provides a method for in vitro producing ICA and its analogs in a one-pot reaction. In the present invention, the plasmid containing the DNA encoding L-amino acid oxidase is transformed into an *E. coli* strain, which is then incubated until $OD_{600}$ being 0.3-0.7. Preferably, the L-amino acid oxidase is NokA of *Nocardiopsis* sp. K-252. After adding an inducing agent, the bacterial culture is further incubated at a 25-40° C. Then, the culture pellet is collected and further re-suspended in a buffer solution to be lyzed by a homogenizer (e.g. French press) or sonication, such that the crude enzyme extract is obtained. Preferably, the buffer solution is Tris, HEPES, MOPS, $K_2HPO_4$ or MES, the pH value of the buffer solution is in the range from 5 to 10, and the glycerol concentration of the buffer solution is 0-25%.

Subsequently, the crude enzyme extract is mixed with an L-tryptophan analog of formula (III), wherein R=H, OH, F, Cl, Br or $CH_3$. The enzymatic biosynthesis is performed at 4-40□.

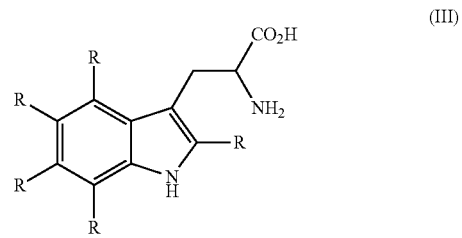

Biochemical characterization and substrate specificity of the gene cluster for biosynthesis of K-252a and its analogs by in vitro heterologous expression system of *Escherichia coli* has been published on Mol. BioSyst., 2009, 5, 1192-1203, which is entirely incorporated herein by reference.

Embodiment of In Vitro Biosynthesis of K252d:

Construction of the NokL Expression Plasmid

FIG. 1 shows the construct map of pCY16. The gene nokL (SEQ ID NO: 1) of *Nocardiopsis* sp. K-252 was amplified on pJC3B5 by PCR with a forward primer with an NdeI site and a reverse primer with a stop codon (TGA) followed by an EcoRI site near 5'-end. The amplified PCR product was ligated with blunt-ended pUC19 (NEB) at SmaI to generate pCY15. After digestion of pCY15 with NdeI and EcoRI, the digestion fragment carrying nokL was cloned into pET21b vector to give pCY16 for the wild-type NokL expression experiments. For plasmid construction of N-terminal $His_6$-tagged NokL, the same digestion fragment was cloned into pET28a to afford pCY17. For C-terminal $His_6$-tagged NokL expression, the nokL gene was amplified on pCY16 by PCR with primer pairs of NKLNdF1 (forward, with NdeI) and NKLXR1 (reverse, with XhoI). The resulting PCR product was subsequently cloned into pET21b at the corresponding sites to yield pMS4.

Preparation of the NokL Cell-Free Crude Extract

The pCY 16 (NokL) and pG-KJE7 (chaperones) plasmids were co-transformed into *E. coli* BL21 (DE3). Cells were grown at 37° C. in LB medium with antibiotics (100 μg/ml ampicillin and 30 μg/ml kanamycin) until $OD_{600}$ reached 0.5. After induction with 0.1% (w/v) L-arabinose and 1 mM IPTG, the culture was allowed to grow at 300 for additional 20 hours. All procedures for the preparation of cell-free crude extract were carried out on ice or at 40. The cells were harvested by centrifugation (3200 g, 15 min), followed by resuspension with potassium phosphate buffer (20 mM $K_2HPO_4$, pH 7.8, 15% glycerol). Cells were broken and disrupted by two passages through a French press cell (Spectronic Instruments) at 16 000 psi. After removal of cell debris by centrifugation at 16000 g for 20 min, the desired crude NokL enzyme extract was obtained for the following enzymatic reaction.

Production of K-252d from Cell-Free Enzymatic Reaction

The crude NokL enzyme extract (1 mL, 20 mM $K_2HPO_4$ at pH 7.8, 15% glycerol) was mixed with TDP-glucose (1.5 mM, 1 mL, 12 mM Tris-HCl, pH7.6, 9% glycerol), K-252c (1.27 mM, 1 mL, 50% DMSO), $MgCl_2$ (12 mM, 1 mL in $H_2O$), and then the pH of the mixture was adjusted to 9.0 (12 mM $MgCl_2$, 50 mM $K_2HPO_4$). The reaction of the mixture was performed at 30□ for 24 hours.

Identification of NokL Enzymatic Product (K252d)

After the enzymatic reaction, the above reaction mixture was quenched by 5 ml of the ice-cold alcohol solution (MeOH-EtOH). The resulting mixture was subsequently subjected to centrifugation (16,000 g, 4□) for 2 hours to remove precipitated proteins. The supernatant was purified by semi-preparative RP-HPLC. Fractions containing K252d were pooled and evaporated to remove organic solvents, followed by extraction with ether. The ether layer containing K252d was evaporated to remove ether and then vacuumed to gain the K252d (2.0 mg). The purity of K252d was greater than 95% as judged by analytical RP-HPLC. The NMR spectrum of K252d dissolved in $D_4$-methanol ($CD_3OD$) was recorded at 500 MHz. For NMR analysis: $^1$H-NMR ($CD_3OD$, 500 MHz) $\delta_H$ 1.80 (3H, d, J=7.0 Hz), 4.15 (1H, dd, J=4.0 Hz), 4.33 (1H, td, J=4.0 Hz), 4.55 (1H, m), 4.70 (1H, d, J=4.0 Hz) 5.05 (2H, d, J=4.0 Hz), 6.54 (1H, d, J=10.0 Hz), 7.26 (1H, t, J=7.0 Hz), 7.30 (1H, t, J=8.5 Hz), 7.45 (1H, t, J=8.0 Hz), 7.48 (1H, t, J=8.5 Hz), 7.61 (1H, d, J=8.5 Hz), 7.72 (1H, d, J=8.5 Hz), 8.02 (1H, d, J=8.5 Hz), 9.40 (1H, d, J=8.0 Hz) ppm. $^{13}$C-NMR ($CD_3OD$, 125 MHz) $\delta_C$ 15.8, 47.0, 68.7, 73.3, 73.6, 78.5, 78.6, 110.5, 112.3, 116.5, 118.9, 119.7, 120.7, 121.0, 121.9, 123.6, 124.1, 126.2, 126.5, 126.8, 129.0, 129.7, 134.5, 141.0, 142.2, 175.8 ppm. For high resolution MALDI-TOF spectrometric analysis: $C_{26}H_{23}N_3O_5$ molecular weight calculated as 457.163, and found m/z of 457.177 [M]$^+$. Upon $^1$H-NMR, $^{13}$C-NMR and COSY, the rhamnosylated product was fully assigned with chemical shifts, in excellent agreement with those of K-252d reported by Yasuzawa (J. Antibiot., 1986, 39, 1072-1078).

Figure 2:
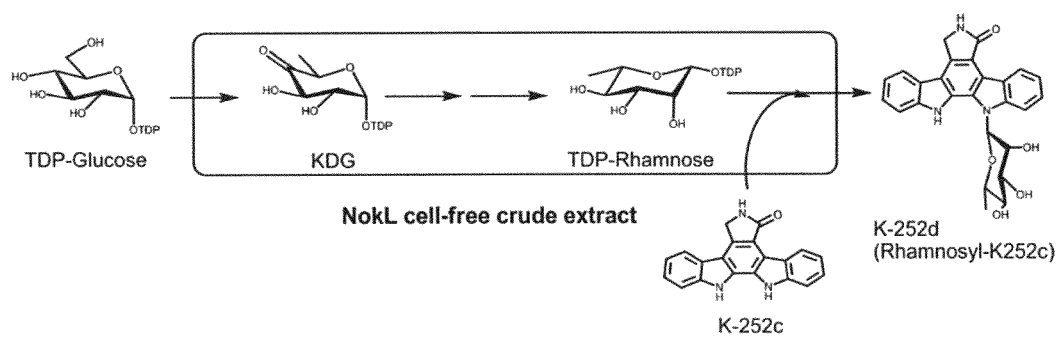
FIG. 2 is a scheme showing synthesis of K-252d according the embodiment of the present invention.

As summarized in the scheme of FIG. 2, the present invention provides a novel method for in vitro producing K-252d in a one-pot reaction without purifying any enzyme. Furthermore, the method of the present invention can produce various indolocarbazole derivatives by using various indolocarbazole aglycones.

Embodiment of In Vitro Biosynthesis of indole-3-carboxaldehyde:

Construction of the NokA Expression Plasmid

Figure 3:
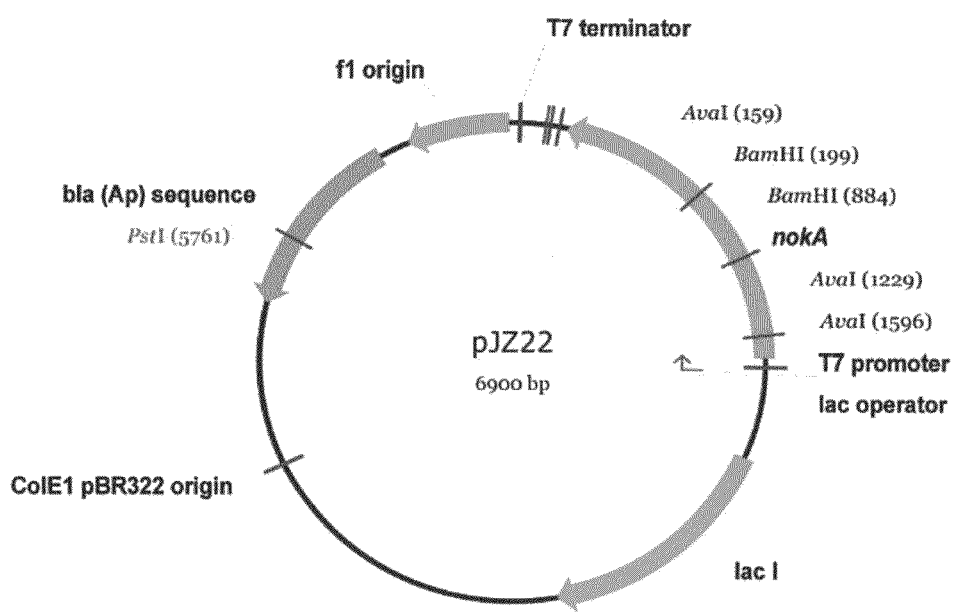
FIG. 3 is a construct map of pJZ22 according to the present invention.

FIG. 3 shows the construct map of pJZ22. The gene nokA (SEQ ID NO: 2) of *Nocardiopsis* sp. K-252 was amplified on pJC3B5 by PCR with a primer pair with NdeI and NheI sites at the 5' and 3' ends, respectively. The amplified PCR product preserving the stop codon was cloned into the NdeI and NheI sites of pET21b to generate pJZ22.

Preparation of the Noka Cell-Free Crude Extract

The pJZ22 (NokA) and pG-KJE7 (chaperones) plasmids were co-transformed into *E. coli* BL21 (DE3). Cells were grown at 37□ in LB medium with antibiotics (100 µg/ml ampicillin and 30 µg/ml kanamycin) until $OD_{600}$ reached 0.5. After induction with 0.2% (w/v) L-arabinose and 0.25 mM IPTG, the culture was allowed to grow at 30□ for additional 10 hours. All procedures for the preparation of cell-free crude extract were carried out on ice or at 4□. The cells were harvested by centrifugation (1902 g, 20 min), followed by resuspension with the buffer (104 mM Tris-HCl, pH 7.6, 10% glycerol). Cells were broken and disrupted by sonication. After removal of cell debris by centrifugation at 15700 g for 20 min, the desired crude NokA enzyme extract was obtained for the following enzymatic reaction.

Production of indole-3-carboxaldehyde from Cell-Free Enzymatic Reaction

The crude NokA enzyme extract (80 µl, 80 mM Tris-HCl at pH 7.8, 7.6% (v/v) glycerol) was mixed with L-tryptophan (4 mM), and then incubated in a total volume of 104 µl at 30□ for 24 hours.

Identification of NokA Enzymatic Product (indole-3-carboxaldehyde)

After the enzymatic reaction, the above reaction mixture was quenched by an equal volume of ice-cold MeOH, and was then subjected to reverse phase RP-HPLC analysis using by Agilent 1100 HPLC series equipped with quaternary pump and diode-array detector. As a result, RP-HPLC analysis of the NokA reaction revealed a major product peak and two minor ones. Upon characterization by NMR and mass spectroscopy, the major product was found to be indole-3-carboxaldehyde (ICA). $^1$H-NMR ($CD_3OD$, 500 MHz), $\delta_H$ 7.170 (1H, ddd, J=1, 7.5 Hz), 7.212 (1H, ddd, J=1.5, 8 Hz), 7.410 (1H, d, J=8 Hz), 8.031 (1H, s), 8.091 (1H, d, J=8 Hz), and 9.822 (1H, s) ppm. $^{13}$C-NMR ($CD_3OD$, 125 MHz), $\delta_C$ 113.122, 120.132, 122.384, 123.611, 124.998, 125.722, 138.940, 139.673, and 187.406 ppm.

Figure 4:
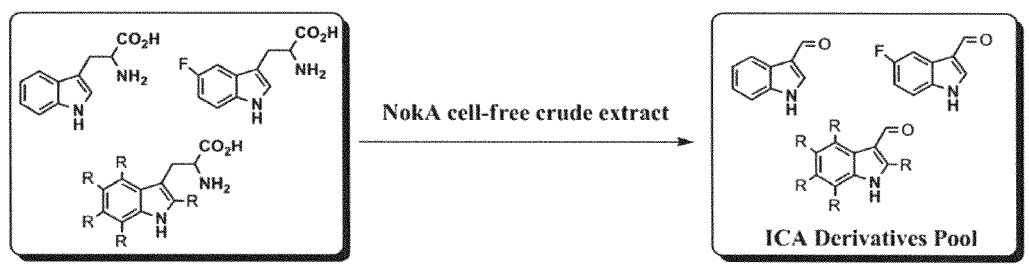
FIG. 4 is a scheme showing synthesis of indole-3-carboxaldehyde analogs according the embodiment of the present invention.

As summarized in the scheme of FIG. 4, the present invention provides a novel method for in vitro producing ICA derivatives in a one-pot reaction without purifying any enzyme.

The invention has been described using the exemplary preferred embodiment. However, it is to be understood that the scope of the invention is not limited to the disclosed arrangements. The scope of the claims, therefore, should be accorded the broadest interpretation, so as to encompass all such modifications and similar arrangements.

What is claimed is:

1. A method for in vitro producing a rhamnosylated indolocarbazole compound, comprising the steps of:
    transforming a plasmid carrying a gene encoding N-glycosyltransferase into a bacterial strain;
    expressing the gene encoding N-glycosyltransferase in the bacterial strain;
    lysing the bacterial strain to obtain a crude enzyme extract; and
    adding thymidine diphosphate (TDP)-glucose, an indolocarbazole aglycone and a metal ion in the crude enzyme extract for performing an enzymatic reaction to form the rhamnosylated indolocarbazole compound,
    wherein the N-glycosyltransferase is NokL of *Nocardiopsis* sp. K-252.

2. The method of claim 1, wherein the bacterial strain is an *E. coli* strain.

3. The method of claim 2, wherein the *E. coli* strain is incubated at 25-40° C.

4. The method of claim 1, wherein the step of lysing is performed by a homogenizer or sonication.

5. The method of claim 1, wherein the bacterial strain is lysed in a buffer selected from the group consisting of Tris buffer, HEPES buffer, MOPS buffer, $K_2HPO_4$ and MES buffer.

6. The method of claim 5, wherein pH of the buffer is in a range from 5 to 10.

7. The method of claim 5, wherein the buffer contains 0-25% of glycerol.

8. The method of claim 1, wherein the indolocarbazole aglycone is a compound of formula (I) or a compound of formula (II),

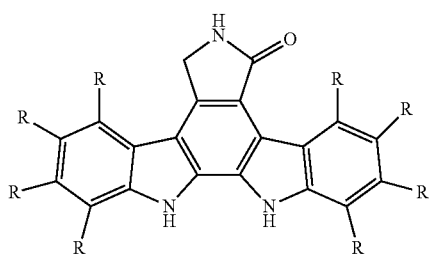

(I)

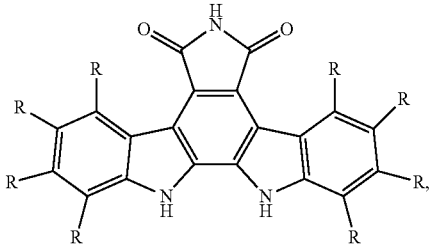

(II)

in which R=H, OH, F, Cl, Br or $CH_3$, and wherein the rhamnosylated indolocarbazole compound is K-252d.

9. The method of claim 1, wherein the metal ion is a magnesium ion or a manganese ion.

10. The method of claim 1, wherein the enzymatic reaction is performed at 4-40° C.

* * * * *

SEQUENCE LISTING

```
<160> NUMBER OF SEQ ID NOS: 2

<210> SEQ ID NO 1
<211> LENGTH: 1314
<212> TYPE: DNA
<213> ORGANISM: Nonomuraea longicatena K252T
<220> FEATURE:
<221> NAME/KEY: gene encoding N-glycosyltransferase
<222> LOCATION: (1)..(1314)
<300> PUBLICATION INFORMATION:
<301> AUTHORS: Hsien-Tai Chiu, Yi-Lin Chen, Chien-Yu Chen, Chyn Jin,
      Meng-Na Lee, Yu-Chin Lin
<302> TITLE: Molecular cloning, sequence analysis and functional
      characterization of the gene cluster for biosynthesis of K-252a
      and its analogs
<303> JOURNAL: Mol. BioSyst.
<304> VOLUME: 5
<306> PAGES: 1180-1191
<307> DATE: 2009-08-04
<308> DATABASE ACCESSION NUMBER: ACN29718
<309> DATABASE ENTRY DATE: 2009-10-06
<300> PUBLICATION INFORMATION:
```

<301> AUTHORS: Hsien-Tai Chiu, Yu-Chin Lin, Meng-Na Lee, Yi-Lin Chen, Mei-Sin Wang, Chia-Chun Lai
<302> TITLE: Biochemical characteriazation and susbstrate specificity of the gene cluster for biosynthesis of Escherichia coli
<303> JOURNAL: Mol. BioSyst.
<304> VOLUME: 5
<306> PAGES: 1192-1203
<307> DATE: 2009-08-04
<308> DATABASE ACCESSION NUMBER: ACN29718
<309> DATABASE ENTRY DATE: 2009-10-06
<300> PUBLICATION INFORMATION:
<301> AUTHORS: Hsien-Tai Chiu, Yu-Chin Lin, Meng-Na Lee, Yi-Lin Chen, Mei-Sin Wang, Chia-Chun Lai
<302> TITLE: Biochemical characteriazation and susbstrate specificity of the gene cluster for biosynthesies of K-252a and its analogs by in vitro heterologous expression system of Escherichia coli
<303> JOURNAL: Mol. BioSyst.
<304> VOLUME: 5
<306> PAGES: 1192-1203
<307> DATE: 2009-08-04
<308> DATABASE ACCESSION NUMBER: ACN29718
<309> DATABASE ENTRY DATE: 2009-10-06

<400> SEQUENCE: 1

```
atgttggcac acgttctgat cgcgacgacc ccggctgacg gccacgtcaa cccggtggtc      60
ccggtcgcgc ggaacctggt gcgcgccggc cacgacgtgc gctggtacac cggagacggc     120
taccggagca agatcaccgc cgtcggcgcg cggcatctgc cgatgttcgc ggcgcacgac     180
ttctccgggc agagcaaggc cgaggcgttc ccgcccaggc ccggctcacc ggcgcggcg      240
agtttcgtcg cggggatgcg ggacatcttc taccgcaccg cgccggacca gatggacgac     300
ctgctccggg tgctggaccg gttccccgcg gacgtgctgg tgtccgacga catgtgctac     360
ggcgcgagct tcgccgccga gcacaccggg ctgccgcacg tgtggatcgg caactcgatc     420
tacgtgctgg gcagccgcga caccgctccg ctcgggcgcg gcctcggccc ctcggcgacg     480
cgggcgggcc ggttgcgcaa cgccgtgctc gcctgggcgg gcgatcacat catgctgcgc     540
gggctgcggc gggcggccga cgcggcccgc gcgcaggcgg ggctgccccg cctgcgcgcg     600
ggcgggatgg agaacatcgc ccgccgtccc gaccgctatc ttgtgggcac cgtcgccgag     660
ctggagttcc cgcgctccga cctgttcgcg ggcacgcact tcgtcggcgc gctcgacctg     720
ccgccgtcgg acacggcctt cgacccgccg ccgtggtggg aggagctgcg cggcgagcgg     780
ccggtcgtgc tggtcacccca gggcacgatc gccgacgacg cgcgccggct gctcctgccc     840
gcgatccggg cgctcgccga cgaaccggtg ctggtcgtcg tgaccaccgg caaccgcacg     900
ctcggcccga gcgccgggac gctgcccgcg aacgtgcggg tggagggctt cgtgccgtac     960
caccggctgc tgccgtacgt ggacgtcatg gtcaccaacg gcggcttcaa cggcgtcacg    1020
gcggcgctca ggcacggcgt cccgctggtc gtcgccgggg ccacggagga gaaggcggac    1080
gtggccgccc gggtggcgta cgcgggtgcc ggggtggcgc tgcgggggc gcggctcgcc    1140
ccggagcggg tgcgcgccgc cgtacgggcg gtgctggacg gcccggagca ccgggccgcc    1200
gcggcccggc tgcacgacgc cttcgcccgg cacgacggcc cgcgccgggc cgccgagctg    1260
atcgaggaac tgatccccgc ccgcaccgcg cccgccaccg gaggcccgct gtga          1314
```

<210> SEQ ID NO 2
<211> LENGTH: 1461
<212> TYPE: DNA
<213> ORGANISM: Nonomuraea longicatena K252T
<300> PUBLICATION INFORMATION:
<301> AUTHORS: Hsien-Tai Chiu, Yi-Lin Chen, Chien-Yu Chen, Chyn Jin, Meng-Na Lee, Yu-Chin Lin
<302> TITLE: Molecular cloning, sequence analysis and functional characterization of the gene cluster for biosynthesis of K-252a and it analogs -continued

```
<303> JOURNAL: Mol. BioSyst.
<304> VOLUME: 5
<306> PAGES: 1180-1191
<307> DATE: 2009-08-04
<300> PUBLICATION INFORMATION:
<301> AUTHORS: Hsien-Tai Chiu, Yu-Chin Lin, Meng-Na Lee, Yi-Lin Chen,
        Mei-Sin Wang, Chia-Chun Lai
<302> TITLE: Biochemical characterization and susbstrate specificity of
        the gene cluster for biosyntheses of K-252a and it analogs by in
        vitro heterologous expression system of Escherichia coli
<303> JOURNAL: Mol. BioSyst.
<304> VOLUME: 5
<306> PAGES: 1192-1203
<307> DATE: 2009-08-04

<400> SEQUENCE: 2
atgttcagtc gtctaccgaa tgtgcgggag ccccggcggg tcaccgtact gggcgcgggc      60
gtggcggggc tggtcgccgc ctacgagctg aacggctcg ggcatcaggt ggagatcatc     120
gaggcggccg accgggtcgg cggccgtgtt cacacgcacc ggttcggttc ggccccccggc    180
gccccgttcg ccgacctggg cgcgatgcgg ctgcgcaccg accacacgcg taccctgcac     240
tacgtcgtcg agctgggcct gcacaacgac atccgcagt tccgcacgct gttcgccgac      300
gacggcaacc tgctgtcgat ccacgacgag cggcacatca gggtgcgcga ggccccggac     360
gtgctcaccg gcaggctcgc ggcacggctc ggcgaccact cctaccggcc ggccacgctg     420
ctgttcgggg cgtggctgca cgcgtgcctg gaggccatcg cgccccggga cttcaacgac     480
tggccggagg tcaccaccga actgctcgat ctggtcgacg gcatcgacct ggagccgtac     540
ctgcaccccg ccgggtccaa accggacctg tacgccgtgg tgaaggacca cccgcagatc     600
cgctcaggac ccttcagagg ccgcgagcgg ctgctggacg acgtcctgga cgagaccagc     660
cccgcgctct accggctgcg cggcggcatg gagacgctca cgaacgcgct ggccgcgcgc     720
atccagggcc ccatctggct gaaccaggag gtgaccggga tcgcggtgca cgacgacggc     780
gtggcggtcg gcgtccggcg cggcggccgg atccgctacc ggaactacga ccacgtactg     840
tgcaccatcc cgttcaccgt gctgcgcggc ctgcggctcg acgggttcga cgcggacaag     900
ctcgccgccg tccacgagac ccagtactgg ccggcgacca agatcgcgct gcgctgccgc     960
gagccgttct gggccgccga cggcatcgcc ggcggcgcct cgttcaccgg cgggctggtc    1020
cgccagacct actacccgcc cgtcgagggc gacccggcgc agggcgcggt gctgatcgcc    1080
agctacacca tcggcccgga cgccgaggcg ctgggcaggc tcgacccggc cgcccgccga    1140
caggtggtcc tggacgaggt cgcccggatg caccccggcc tgcgggagcg cggcatgatc    1200
ctcgacaccg ccggccgcgc gtggggcgaa caccggtgga gcctgggcgc ggccaccatc    1260
cgctggggcc aggacgccgg cacccgcaag gagcagcagt gggcggcggc ccggccgcag    1320
ggcaggctgt tcttcgcggg cgagcactgc tcgtccatgc cggcctggat cgagggcgcg    1380
atcgagtcgg tcaccgacgc gctgcgcgac atggagaccc gcgacccgca cgaactgatg    1440
cggctggatc tgggccgatg a                                              1461
```